United States Patent [19]

Hochstrasser et al.

[11] Patent Number: 5,283,196
[45] Date of Patent: Feb. 1, 1994

[54] POLYACRYLAMIDE GELS WITH IMPROVED DETECTION OF PROTEIN

[75] Inventors: Denis F. Hochstrasser, Geneva, Switzerland; Carl R. Merrill, Rockville, Md; Abraham Patchornik, Ness-Ziona, Israel

[73] Assignee: The United States of America as represented by the Department of Health and Human Services, Washington, D.C.

[21] Appl. No.: 789,456

[22] Filed: Nov. 7, 1991

Related U.S. Application Data

[63] Continuation of Ser. No. 159,847, Feb. 24, 1988, abandoned, which is a continuation-in-part of Ser. No. 142,978, Jan. 12, 1988, abandoned.

[51] Int. Cl.$^5$ .................. G01N 30/00; G01N 33/68
[52] U.S. Cl. ........................... 436/86; 436/94; 436/161; 436/178; 204/182.6; 204/182.8
[58] Field of Search ............. 204/181, 182.2, 182.4, 204/182.6, 182.8; 436/86–90, 178, 94, 161; 544/387

[56] References Cited

U.S. PATENT DOCUMENTS

| | | | |
|---|---|---|---|
| 4,189,370 | 2/1980 | Boschetti | 204/299 R |
| 4,421,915 | 12/1983 | Ponticello et al. | 544/387 |
| 4,535,010 | 8/1985 | Axen et al. | |
| 4,555,490 | 11/1985 | Merril | 436/86 |
| 4,654,132 | 3/1987 | Takagi et al. | 204/182.8 |
| 4,874,490 | 10/1989 | Hochstrasser | 204/182.1 |
| 4,892,814 | 1/1990 | Harrington et al. | 435/5 |

OTHER PUBLICATIONS

Artoni et al., *Analytical Biochemistry* 137: 420–428, 1984.

*Primary Examiner*—James C. Housel
*Assistant Examiner*—David Redding
*Attorney, Agent, or Firm*—Lowe, Price, LeBlanc & Becker

[57] ABSTRACT

Amine-acryloyl and -methacryloyl derivatives and 1,6-heptadiene-4-ol can be used to provide crosslinked polyacrylamide gels which are useful in protein and nucleic acid separation and detection. The gels crosslinked with the compounds of the present invention exhibit much less background silver staining than previously known acrylamide gels.

8 Claims, 4 Drawing Sheets

| SOLUTION NUMBER | STOCK SOLUTION | TOTAL ACRYLAMIDE CONCENTRATION | CROSSLINKER RATIO | SILVER STAINED GEL (5 min DEVELOPMENT TIME) |
|---|---|---|---|---|
| 1. | A | 20% T | 0.5% C |  |
| 2. | B | 20% T | 2.7% C |  |
| 3. | A | 10% T | 0.5% C |  |
| 4. | B | 10% T | 2.7% C |  |
| 5. | C | 10% T | 5.0% C |  |

| SOLUTION NUMBER | STOCK SOLUTION | TOTAL ACRYLAMIDE CONCENTRATION | CROSSLINKER RATIO | SILVER STAINED GEL (5 min DEVELOPMENT TIME) |
|---|---|---|---|---|
| 1. | A | 20% T | 0.5% C | |
| 2. | B | 20% T | 2.7% C | |
| 3. | A | 10% T | 0.5% C | |
| 4. | B | 10% T | 2.7% C | |
| 5. | C | 10% T | 5.0% C | |

| SOLUTION NUMBER | STOCK SOLUTION | TOTAL ACRYLAMIDE CONCENTRATION | CROSSLINKER RATIO* | SILVER STAINED GEL (20 min DEVELOPMENT TIME) |
|---|---|---|---|---|
| 6. | D (DHEBA) | 10 % T | 2.7 % C | |
| 7. | E (DATD) | 10 % T | 2.7 % C | |
| 8. | F (ED) | 10 % T | 2.7 % C | |
| 9. | G (BIS$_1$) | 10 % T | 2.7 % C | |
| 10. | D (DHEBA) | 20 % T | 2.7 % C | |
| 11. | E (DATD) | 20 % T | 2.7 % C | |
| 12. | F (ED) | 20 % T | 2.7 % C | |
| 13. | G (BIS$_1$) | 20 % T | 2.7 % C | |

*APPROXIMATIVE VALUE FOR COMPARISON WITH BIS$_1$ (19)

FIG. 2

| Solution no. | Stock solution | Crosslinking agent or related compound | Total concentration and ratio[a] | | Development time (min) | |
|---|---|---|---|---|---|---|
| | | | | | 5 | 30 |
| 14. | J | methylene-bisacrylamide | 13% T | 2.7% C | | |
| 15. | K | methylene-bisacrylamide * | 13% T | 2.7% C | | |
| 16. | L | diacrylyl-piperazine~ | 13% T | 2.7% C | | |
| 17. | M | (16.)+ acrolein-dimethylacetal | 13% T | 2.7% C | | |
| 18. | N | (16.)+ acrylic acid | 13% T | 2.7% C | | |
| 19. | O | ethylene-diacrylate + 5% of diacrylyl-piperazine | 13% T | 2.7% C | | |

FIG. 3 a. LIGHT BOX ALONE b. 2-DGE OF PLASMA SAMPLE; POLYACRYLAMIDE GEL POLYMERIZED WITH DIACRYLYIPIPERAZINE (PIP)

c. LEFT SIDE OF AN IDENTICAL 2-DGE; GEL POLYMERIZED WITH METHYLENEBISACRYLAMIDE (BIS)

POLYACRYLAMIDE GELS WITH IMPROVED DETECTION OF PROTEIN

This application is a continuation of application Ser. No. 07/159,847 filed on Feb. 24, 1988, which is a CIP of application Ser. No. 07/142,978 filed Jan. 12, 1988, both now abandoned.

FIELD OF THE INVENTION

The present invention relates to the crosslinking of gels and resins, and especially relates to crosslinking agents for polyacrylamide gels which are useful in separating proteins and in the silver stain detection of proteins and nucleic acids.

BACKGROUND OF THE INVENTION

The formation of background staining has limited the sensitivity, reproducibility, and quantitative analyses of most polyacrylamide silver staining methods. In the first applications of silver staining as a detection method for proteins separated on polyacrylamide gels, the problem of excessive background was addressed. A photographic "reducer" containing sodium thiosulfate was used to reduce the excessive background staining. However, this procedure not only affected the background, but also the silver densities in the stained protein bands or spots. Furthermore, the "reducer" effect on protein bands or spots is not necessarily proportional. This non-proportional loss of silver grains has limited this use of thiosulfate, particularly in quantitative applications.

It was found that background staining of the ammoniacal silver stain could also be reduced by pretreating the gels with diluted thiosulfate solutions prior to silver reduction or image development. However, such pretreatment often results in the inability to visualize trace proteins. The use of thiosulfate to eliminate background staining also results in another problem, i.e. the loss of image permanence.

SUMMARY OF THE INVENTION

Polyacrylamide gels formed from the crosslinking agents of the present invention, have been found to produce very little, if any, background staining. The key observations which permitted this development were: the essential nature of basic and sulfur containing amino acids in the detection of peptides by the silver staining reaction, evidence that the active groups in the basic amino acids, the imidazole, guanidine, and amino groups, or the sulfur groups in the sulfur containing amino acids, require cooperative effects. That is, they function poorly when they are isolated in a polymer, but if two or more basic amino acids or sulfur containing amino acids are in close proximity, a good staining reaction will occur. These observations, which indicate the need for cooperative effects between the active amino acids, have been corroborated by staining studies in which basic amino acids were separated by varying distances in a series of synthetic polymers.

It is an object of the present invention to overcome deficiencies in the prior art, and also deficiencies outlined above.

It is a further object of the prior invention to provide for improved stain detection.

It is yet a further object of the present invention to provide for improved cross-linking of polymeric gels.

It is another object of the present invention to provide polyacrylamide gels which can be used for separating proteins and nucleic acids.

It is yet another object of the present invention to provide polyacrylamide gels which can be used for silver staining proteins and nucleic acids.

It is still another object of the present invention to provide crosslinking agents for polyacrylamide gels which are useful in separation and silver staining of proteins and nucleic acids.

Studies on the mechanisms of silver stains led to the discovery that the amide groups in the methylene-bisacrylamide crosslinking agent might be responsible for the background found with the silver stains. Methylenebisacrylamide contains two amide groups which are separated by a single carbon atom.

It has now been found that the appearance of background staining depends mainly on the presence and position of amido groups in the crosslinking agents, as well as on the presence of other groups, in the crosslinker or on the acrylamide chain, particularly on hydroxyl and keto groups. Carboxyl, hydroxyl, imidazole, and other groups may have effects on the oxidation-reduction potential, or in some cases on the internal pH of the gel, which would affect the rate of reduction of ionic to metallic silver. These findings applied as well to Coomassie blue staining.

The crosslinking agents of the present invention are polymerizable amine acryloyl and methacryloyl derivatives of compounds having at least one secondary amine which forms a tertiary amide group. The compounds may contain more than one acryloyl group, or more than one tertiary amide group. In addition to the amine acryloyl and methacryloyl derivatives, 1,6-heptadiene-4-ol has also been found to be a particularly effective crosslinking agent for polyacrylamide gels.

Some of the crosslinking agents of the present invention have the following formulae:

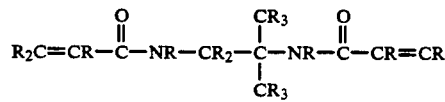

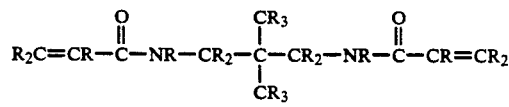

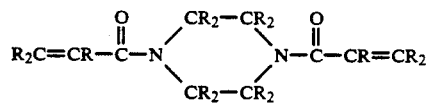

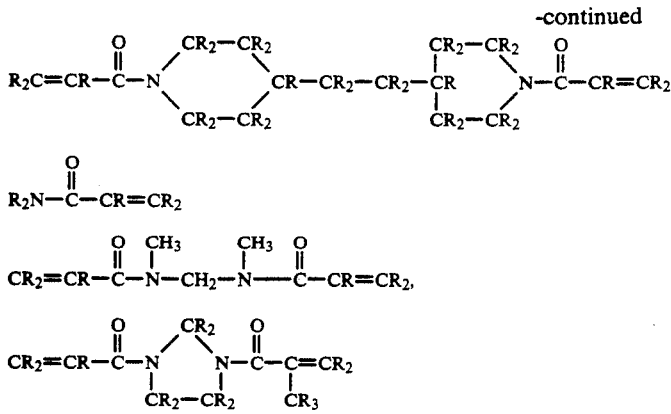

wherein R can be H, methyl, ethyl, propyl, isopropyl, or butyl.

The crosslinkers of the present invention are particularly useful for preparing polyacrylamide gels for separating proteins and nucleic acids and for detection of proteins and nucleic acids. The gels which can be crosslinked using the crosslinking agents of the present invention include any acrylamide gels which are commonly used for separation or silver staining of proteins and nucleic acids. The crosslinkers are used in amounts ranging from about 1% to about 20% by weight of the acrylamide to be crosslinked.

To prepare gels according to the present invention, the monomer and crosslinker are dissolved in water or a solvent which can dissolve both the monomer and crosslinker, and polymerization is initiated with a conventional initiator, such as ammonium persulfate.

BRIEF DESCRIPTION OF THE DRAWINGS

FIG. 2 shows the effect of different crosslinking agents on silver staining in polyacrylamide gels: the band formed by the crosslinking agent lacking amide groups, ED, did not show any background with silver staining. DATD, BIS and DHEBA gave, by increasing order, a light to dark background. In fact, gels with DHEBA as the crosslinking agent turned black within a few minutes in ammoniacal silver nitrate solution. It may be that the hydroxyl groups in this compound are active in the reduction of ionic to metallic silver. The possible relative alkalinity of the gel produced with this crosslinker may play an even more important role in the reduction of silver ions. In this respect, TEMED which is an organic base enhances background staining, while the incorporation of acrylic acid in the gel reduces background staining. ED could be used as secondary crosslinking agent to make porosity gradient. It does not give any background.

FIG. 3 shows the effect of the new crosslinking agents (PIP) and adjunct compounds of the present invention on silver staining in polyacrylamide gels: the band formed by the PIP crosslinking agent did not show any background with silver staining after 5 min development time and a yellow background after 30 min development time, while bands, polymerized with BIS, were black and opaque. PIP alone or even more with acrylic acid gave by far the least background. Gels were achieved with acrylic acid with no background Coomassie blue staining also.

DETAILED DESCRIPTION OF THE INVENTION

Figure 1:
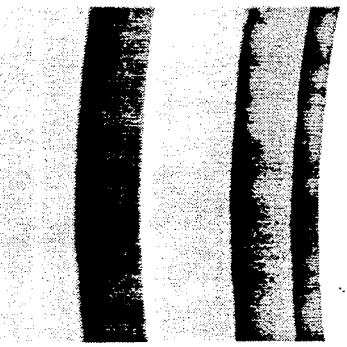
FIG. 1 shows the effects of methylene-bisacrylamide (BIS) crosslinking agent on silver staining in polyacrylamide gels: the background intensity is mostly proportional to the amount of BIS polymerized in the gel. It explains why the background staining in porosity gradient gels is uneven. Development was stopped after 5 min to show the maximum contrast.
Figure 4:
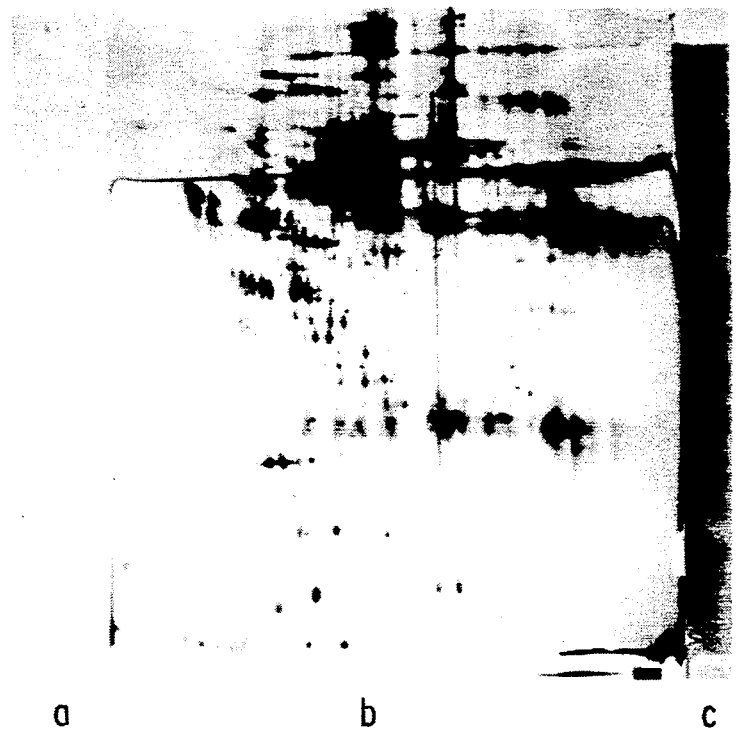
FIG. 4 shows a high resolution silver stained two-dimensional gel electrophoresis of 0.3 ul plasma sample. The low level of background is striking, especially after this development time (3 min). An identical gel, but with BIS as the crosslinking agent, was much darker (right hand wide of the picture). Computerized scan of the two gels using an Eikonix digital scanner showed that the BIS crosslinked gel had a mean background of approximately 0.25 OD (optic density value) while the PIP gel had a background of less than 0.03 OD. In other words, the lower "gray" value was 50/255 with a mean value of 111/255 for the gel polymerized with BIS and 0/255 with a mean value of 15/255 for the gel polymerized with PIP. The improved protein separation, particularly in the high molecular weight and basic regions, was evident. This allowed the detection of 10% more spots with the same detection algorithm, because of better protein separation and spot definition (23,24). There was less vertical streaking due to better protein transfer from the first (IEF) to the second (SDS) dimension. This new crosslinking agent should allow more reproducible quantitative results. It suppressed the phenomenon called "doughnut effect"; highly concentrated proteins tend to have an inverse staining in their spot center which eventually turns black after a prolong development time. The pictures did not fade over time.

A series of new crosslinking agents for polyacrylamide gels has been developed. The use of these crosslinking agents for preparing polyacrylamide gels for protein and nucleic acid separation and detection prevents background staining. The gels prepared using the crosslinking agents of the present invention provide improved reproducibility and accuracy in the separation and detection of proteins and nucleic acids by silver staining techniques.

In the following examples, the stock solutions were prepared by dissolving acrylamide and N,N'-methylene-bisacrylamide in water in the following amounts: stock solution A contained 30 grams and 0.15 g; B contained 29.2 grams and 0.8 g, and C contained 28.5 g and 1.5 g, respectively. These stock solutions were each adjusted with water to a final volume of 100 ml and gave respectively a crosslinking ratio of 0.5, 2.7, and 5%.

Solutions for the polymerization of the gels were prepared: solution 1 contained 6 ml of stock A and 3 ml of water; solution 2 contained 6 ml of stock B and 3 ml of water; solutions 3, 4, and 5 contained 6 ml of water and 3 ml of each of the stock solutions A, B, and C, respectively. TEMED in 10 microliter aliquots was added to each of the five gel solutions above, and these were then mixed and degassed. Polymerization was initiated sequentially by the addition of 100 microliters of ammonium persulfate stock solution (10 g/100 ml of water) to each of the five gel solution.

The gel was cast by gently pouring 4 ml of each of the solutions in inverse sequential order, beginning with solution 5 between two glass plates separated by 1.5 mm spacers, at 4 minute intervals. The stepwise composite gel, a "zebra" gel, was removed from between the glass plates two hours later and stained as described in Protein detection Studies with gels made from previously known crosslinkers, as shown in FIG. 1a.

Crosslinkers which had been previously synthesized to produce polyacrylamide gels with various properties were incorporated in this study to determine their ability to form gels that would yield little if any background when stained with silver. Four known crosslinkers: methylene-bisacrylamide ($BIS_1$), ethylene-diacrylate (ED), diallyl-tartardiamide (DATD), and dihydroxyethylene-bisacrylamide (DHEBA) were used.

Stock solutions were prepared as follows: solution D contained 30 grams of acrylamide and 1.07 g of DHEBA in 100 ml of water; solution E contained 30 grams of acrylamide and 1.22 g of DATD in 100 ml of water; solution F contained 30 grams of acrylamide and 1.6 g of ED in 100 ml of water; and solution G contained 30 grams of acrylamide and 0.8 g of $BIS_1$ in 100 ml of water. The amount of the different crosslinkers was chosen to obtain similar molecular weight separation or apparent pore sizes on SDS gels.

Solutions for the casting of the gels were prepared: gel bands 6, 7, 8, and 9 contained 3 ml of stocks D, E, F, and G, respectively, each of which was diluted by the addition of 6 ml of water; gel bands 10, 11, 12, and 13 contained 6 ml of stocks D, E, F, and G respectively, each of which was diluted by the addition of 3 ml of water. TEMED in 10 microliter aliquots was added to each of the eight solutions, and these were then mixed and degassed. Poylmerization was initiated by successive addition of 100 microliters of ammonium persulfate stock solution (10 g/100 ml of water) followed by gentle pouring of 4 ml of each of the solutions into the space between two glass plates separated by 1.5 mm spacers, at four minute intervals. The stepwise composite "zebra" gel was removed from between the glass plates two hours later and stained as described in Protein Detection, FIG. 2.

Tetra-, hexa-, nona-, and dodecano-methylene-bisacrylamide were tested for their effect on background staining. Nona and dodecano-methylene-bisacrylamide were poorly soluble, especially dodecano-methylene-bisacrylamide and required temperatures above 60° C. for solubilization. The gels were prepared in a similar manner as the above. Tetra- and hexamethylene-bisacrylamide had to be synthesized or purified using the procedure outlined below.

Two dimensional gel electrophoresis of plasma samples were performed as described below.

The acryloyl or methacryloyl secondary amine derivative crosslinking agents of the present invention are all synthesized in the same general manner. Each crosslinker was formed by reacting a millimole of appropriate anhydrous secondary amine with at least one millimole of acryloyl chloride or methacryloyl chloride to produce an amino-acryloyl derivative compound. This reaction released at least one millimole of hydrochloride, depending upon the number of initial moles of acryloyl or methacryloyl chloride used, which were neutralized by the appropriate amount of triethylamine, which was present in the reaction vessel.

The water of hydrous amine compounds had to be removed by distillation in toluene prior to their use in the synthesis. The amine was then recovered by evaporation of the solvent and redissolved in tetrahydrofuran before being used in the reaction. The hydrochloride molecules of other amines were removed by dissolving the amine-hydrochloride in water, titrating the pH to 14 with 10N NaOH and extracting the amine with chloroform. Water was entirely removed from chloroform by the addition of anhydrous magnesium sulfate, which was then removed by filtration. The chloroform was then evaporated from the filtrate, and the amine was solubilized in tetrahydrofuran.

Tetrahydrofuran was the solvent used for all of the reactions. Although chloroform has traditionally been used as a solvent for this type of reaction, the use of chloroform in the present process resulted in either a low or non-measurable yield of amine-acryloyl derivatives. Hydroquinone was added to prevent an autopolymerization reaction.

To prepare some of the amine-acryloyl crosslinking compounds of the present invention, 21 mmol of triethylamine and 10 mmol of the specific amine for each crosslinker were dissolved in 50 ml of tetrahydrofuran. This solution was cooled in an acetone/ice bath, and 20 ml of a tetrahydrofuran solution containing 20 mmol of acryloyl-chloride was slowly added with constant stirring over a period of twenty minutes. The reaction temperature was monitored and not permitted to exceed 0° C. The reaction vessel was removed from the acetone/ice bath after the addition of the acryloyl-chloride and permitted to equilibrate to room temperature for 15 minutes. This permitted the completion of the reaction. Six mg of hydroquinone was then added to the reaction mixture, which was then filtered through a medium pore sintered glass filter. The precipitate, consisting of amine hydrochlorides, was discarded, and the filtrate was titrated to a pH of 7.0 with 5N HCl. The solution was titrated with HCl and refiltered to remove the newly precipitated free amine compounds.

The final amine-acryloyl derivative compound was extracted from the tetrahydrofuran solvent by countercurrent extraction with petroleum ether. After the extraction, the compound was allowed to crystallize from the petroleum ether at 20° C. The crystals were collected by filtration through a sintered medium pore glass filter. The crystals were then redissolved in fresh tetrahydrofuran, re-extracted, and crystallized from petroleum ether. The overall recovery was greater than 30%.

The amine-acryloyl derivatives that could not be extracted from petroleum ether were purified by evaporating the tetrahydrofuran solvent after neutralization of the amine and removal of the compounds by filtration.

The structure of diacrylyl piperazine was verified by proton NMR spectroscopy and melting point determination.

Gels were formed by using about 30 g of acrylamide and the molar equivalent to 0.8 g of bisacrylamide of the crosslinking agents of the present invention, which were dissolved in a final volume of 100 ml deionized water. Twenty four ml. of this stock solution was mixed with Tris HCl, OH 8.8, 1.5 M solution (14.5 ml), and with 16.5 ml of deionized water. Once 80 microliters of TEMED was added, the solution was degassed, and polymerization was initiated with 300 microliters of 100 g/liter ammonium persulfate.

The gels containing heptadienol as crosslinking agent required a different method of preparation, because of the insolubility in water of this compound. Two stock solutions containing acrylamide were made: stock H contained 30 grams of acrylamide in water, while stock I contained 30 grams of acrylamide in methanol. Heptadienol, 0.5 ml. was mixed with 16.5 ml of stock solution I, and then 24 ml of stock solution H was added. The pH of this solution was then buffered by the addition of 14.6 ml of 1.5 M Tris HCl solution, pH 8.8.

Some of the new crosslinking agents of the present invention were tested individually in "zebra" gels as described above, and were used for 2-DGE separation of plasma samples, except for acetone-bisacrylamide.

To compare the effect on background staining of additional adjunct agents placed in the gel solution prior to polymerization, gels were prepared as follows: stock solution J contained 30 grams of acrylamide and 0.8 grams of methylene bis-acrylamide in a final volume of 100 ml of water; stock solution K contained 30 grams of acrylamide and 0.8 g of highly purified methylene-bisacrylamide in a final volume of 100 ml water; stock solution L contained 30 grams of acrylamide and 1.0 g of diacrylyl-piperazine in a final volume of 100 ml of water; stock solution M contained 30 grams of acrylamide, 1.0 gram diacrylyl-piperazine, and 1.5 g acrolein-dimethyl acetal in final volume of 100 ml water; stock solution N contained 30 grams of acrylamide, 1.0 g diacrylyl-piperazine, and 1.5 g acrylic acid in a final volume of 100 ml water; stock solution 0 contained 30 grams acrylamide, 1.6 grams ethylene-diacrylate, and 50 mg diacrylyl-piperazine in a final volume of 100 ml water.

The amounts of the different crosslinkers were chosen to provide similar molecular weight separation or apparent pore size on SDS gels.

Solutions for the casting of the gels were prepared as follows: solution 14, 15, 16, 17, 18, and 19 contained 24 ml of stock solution J, K, L, M, N, and O respectively, mixed with 14.6 ml of Tris HCl, pH 8.8, 1.5 M, and with 16.5 ml of deionized water. Once 80 microliters of TEMED were added, the six solution were degassed. Polymerization was initiated sequentially with 300 microliters of 100 g/liter ammonium persulfate.

Two dimensional gel electrophoresis offers the greatest electrophoretic resolution currently available. The crosslinking agents were tested for their resolving power in high resolution 2-DGE systems.

The isoelectric focusing and SDS-PAGE gels were prepared according to the method of Hochstrasser, et al., *Electrophoresis* 7, 505–511 (1986) except that the acrylamide/N,N-methylene-bisacrylamide solution (respectively, 30 g and 0.8 g in deionized water, final volume of 100 ml) were replaced by acrylamide/crosslinker solution, respectively 30 grams and 0.8 g $BIS_1$ molar equivalent of tested crosslinking agents in deionized water, final volume of 100 ml. The isoelectric focusing separation was performed with carrier ampholytes and not with immobilized pH gradients.

Of the crosslinking agents tested, tetra- and hexa-methylene bisacrylamide and diacrylyl-piperazine demonstrated sharper bands than the other crosslinking agents. In addition, the diacrylyl-piperazine provided a gel with increased physical strength. This increased strength permitted a decreased total acrylamide concentration, with the resulting increase in pore size, in the first dimension. The total acrylamide concentration in the isoelectric focusing capillary gels was decreased to 3% (T value) with 1% diacrylyl-piperazine crosslinker, which was not possible with acrylamide/$BIS_1$ solution because of poor polymerization. Sample preparation, sample load, and running conditions were as previously published by Hochstrasser et al., ibid.

Silver stain detection of proteins was performed as follows. After the protein separation was completed, the gels were placed for five minutes into water and then into ethanol: acetic acid: water (40:10:50) for one hour, in ethanol:acetic acid: water (5:5:90) for at least three hours or overnight. After a five minute water wash, the gels were soaked for thirty minutes in a 10% glutaraldehyde solution. The glutaraldehyde was removed by extensive water washes, three ten minute washes followed by four thirty minute washes. The ammoniacal silver nitrate solution was prepared by the slow addition of a solution containing six grams of silver nitrate in 30 ml of deionized water to a solution containing 10 ml of ammonium hydroxide, 1.5 ml of 10N sodium hydroxide, and 160 ml water. The final volume was adjusted to 750 ml with deionized water. The gels were soaked in the ammoniacal silver nitrate solution for ten minutes, then washed three times for five minutes with water. The developing solution contained 0.1 g of citric acid and 1 ml of formaldehyde/liter of deionized water. The gels were developed for three minutes or longer in this solution, and were then placed into a solution containing 50 ml acetic acid/1 liter of water for one hour to stop the development. For storage purposes, the acetic acid solution was replaced by a glycerol:ethanol:water(2:10:88) solution.

It was found that those crosslinkers which contain secondary amide groups or amide groups which are totally substituted, i.e., tertiary amide groups produced little if any background staining. Of these compounds, diacrylyl-piperazine is of particular importance because it is easy to synthesize and to purify. Its high solubility in water facilitates its use as a crosslinker in polyacrylamide gels.

These new compounds provide gels which polymerize more quickly than gels with the molar equivalent of N-methylene-bisacrylamide. Diacrylyl-piperazine also provides gels which do not swell as much with water as do current gels prepared with N-methylene-bisacrylamide and which have a slight increase in conductivity. In SDS PAGE separations, there is an apparent decreased pore size when the molar equivalent of diacrylyl-piperazine and N-methylene-bisacrylamide crosslinkers are compared. Diacrylyl-piperazine also provides polyacrylamide gels with apparent increased physical strength. All of these properties permitted the reduction of total acrylamide gels in isoelectric focusing gels to 3%. This reduced acrylamide concentration and slightly increased conductivity improved the isoelectric focusing protein separation and allowed higher protein load on the gels.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method of detecting proteins which comprises:

providing a crosslinked acrylamide gel which crosslinked acrylamide gel is prepared by adding an amine acryloyl derivative of an amino compound having at least one secondary amine group, said derivative having at least one tertiary amide group to a solution of acrylamide and subjecting the acrylamide to crosslinking;

placing a sample containing proteins onto the crosslinked acrylamide gel;

soaking the crosslinked acrylamide gel having the sample containing proteins thereon in an appropriate solvent for causing the proteins to be separated;

permitting the solvent to carry the proteins a predetermined distance through the crosslinked acrylamide gel; and soaking the crosslinked acrylamide gel in a silver solution to develop the crosslinked acrylamide gel and detect the proteins.

2. The method according to claim 1, wherein the amino compound contains two secondary amino groups.

3. The method according to claim 1, wherein said derivative contains two tertiary amide groups.

4. The method according to claim 3, wherein said derivative is diacrylpiperazine or diacrylyl ethylenedipiperidine.

5. The method according to claim 1, wherein said crosslinked acrylamide gel is crosslinked in the presence of an ammonium persulfate initiator.

6. The method according to claim 1, wherein the silver solution is an ammoniacal silver nitrate solution.

7. The method according to claim 1, which further comprises placing the developed gel into an acetic acid/water solution to stop the development.

8. The method according to claim 1, wherein said derivative is

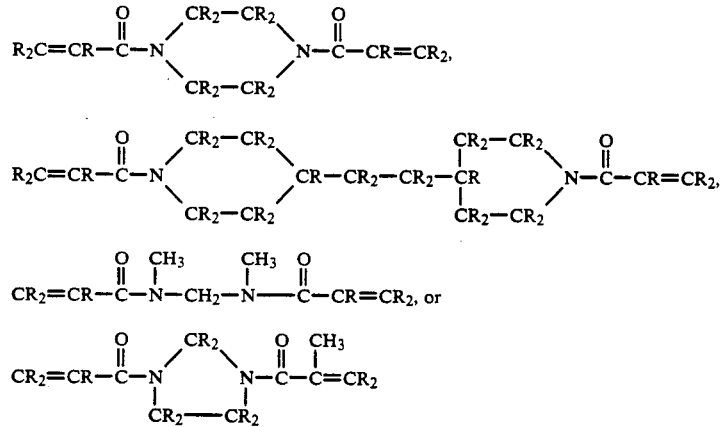

wherein R is selected from the group consisting of H, methyl, ethyl, propyl, isopropyl and butyl.